(12) United States Patent
Kim et al.

(10) Patent No.: US 10,437,035 B2
(45) Date of Patent: Oct. 8, 2019

(54) MICROASPIRATION-BASED LUNG WINDOW APPARATUS FOR OBTAINING MICROSCOPIC IMAGE OF IN VIVO LUNG TISSUE AND METHOD FOR OBTAINING IMAGE USING SAME

(71) Applicants: MEDICINAL BIOCONVERGENCE RESEARCH CENTER, Gyeonggi-do (KR); KOREA ADVANCED INSTITUTE OF SCIENCE AND TECHNOLOGY, Daejeon (KR)

(72) Inventors: Pil Han Kim, Daejeon (KR); Inwon Park, Daejeon (KR); Sunghoon Kim, Seoul (KR)

(73) Assignees: Medicinal Bioconvergence Research Center, Gyeonggi-do (KR); Korea Advanced Institute of Science and Technology, Daejeon (KR)

( * ) Notice: Subject to any disclaimer, the term of this patent is extended or adjusted under 35 U.S.C. 154(b) by 59 days.

(21) Appl. No.: 15/756,478

(22) PCT Filed: Aug. 31, 2016

(86) PCT No.: PCT/KR2016/009720
§ 371 (c)(1),
(2) Date: Feb. 28, 2018

(87) PCT Pub. No.: WO2017/039316
PCT Pub. Date: Mar. 9, 2017

(65) Prior Publication Data
US 2018/0246311 A1 Aug. 30, 2018

(30) Foreign Application Priority Data

Aug. 31, 2015 (KR) .................. 10-2015-0123216

(51) Int. Cl.
*G02B 21/36* (2006.01)
*A61B 5/00* (2006.01)
(Continued)

(52) U.S. Cl.
CPC .............. *G02B 21/362* (2013.01); *A61B 5/00* (2013.01); *A61B 5/0084* (2013.01); *A61B 5/08* (2013.01);
(Continued)

(58) Field of Classification Search
CPC ...... G02B 21/362; G02B 21/00; G02B 21/36; G02B 21/361; G02B 21/0012;
(Continued)

(56) References Cited

U.S. PATENT DOCUMENTS 5,907,425 A * 5/1999 Dickensheets ..... G02B 21/0048
359/201.1
6,414,779 B1 * 7/2002 Mandella ........... A61B 1/00183
359/201.1
(Continued)

*Primary Examiner* — Collin X Beatty
(74) *Attorney, Agent, or Firm* — Leason Ellis LLP

(57) ABSTRACT

Disclosed are a microaspiration-based lung window apparatus for obtaining a microscopic image of in vivo lung tissue and a method for using the window apparatus to obtain cell-level and molecular level microscopic images of in vivo lung tissue while maintaining physiological respiration and circulation of an animal without interference. In one embodiment, a lung window apparatus comprises an open window having the upper and lower parts open, a cover glass placed over the upper part and lung tissue coming in contact with the lower part; an aspiration tube extending from one side of the open window to an aspiration apparatus enabling the inside of the open window to be in a vacuum state; and a tilting mount placing unit extending from one side of the open window having a tilting mount to enable the cover glass and an object lens of a confocal microscope system to stay parallel to each other.

7 Claims, 8 Drawing Sheets

(51) Int. Cl.
*A61B 5/08* (2006.01)
*G02B 21/00* (2006.01)

(52) U.S. Cl.
CPC .......... *A61B 5/0803* (2013.01); *A61B 5/6886* (2013.01); *G02B 21/00* (2013.01); *G02B 21/0012* (2013.01); *G02B 21/36* (2013.01); *A61B 5/0071* (2013.01); *G02B 21/361* (2013.01)

(58) Field of Classification Search
CPC ........ G02B 21/34; G02B 21/26; G02B 21/33; G02B 21/0048; G02B 21/0032; G02B 21/368; G02B 21/0024; G02B 21/0076; G02B 21/367; G02B 21/0004; G02B 21/0036; G02B 21/0052; G02B 21/0064; G02B 21/0084; G02B 21/06; G02B 21/16; G02B 21/002; G02B 21/0028; G02B 21/0068; G02B 21/008; G02B 21/02; G02B 21/082; G02B 21/14; G02B 7/003; G02B 21/004; G02B 21/0044; G02B 21/0056; G02B 21/18; G02B 21/32; G02B 21/365; G02B 23/24; G02B 26/0841; G02B 5/005; G02B 6/065; G02B 6/262; G02B 6/3652; G02B 6/4204; G02B 6/4249; G02B 6/4298; G02B 21/006; G02B 21/0072; G02B 21/0088; G02B 21/0092; G02B 21/086; G02B 21/10; G02B 21/12; G02B 21/22; G02B 21/24; G02B 21/241; G02B 21/245; G02B 23/2453; G02B 23/26; G02B 26/0816; G02B 26/12; G02B 3/0043; G02B 3/005; G02B 5/3083; G02B 6/42; G02B 7/04; G02B 7/36; A61B 5/00; A61B 5/0084; A61B 5/08; A61B 5/0803; A61B 5/6886; A61B 5/0071; A61B 5/0068; A61B 5/0075; A61B 1/043; A61B 5/0066; A61B 5/0062; A61B 1/00165; A61B 1/07; A61B 1/2676; A61B 1/00172; A61B 1/018; A61B 2090/306; A61B 2090/3614; A61B 5/0059; A61B 5/055; A61B 5/4839; A61B 90/36; A61B 1/00096; A61B 2034/2055; A61B 5/0086; A61B 10/0096; A61B 10/02; A61B 10/0233; A61B 10/06; A61B 17/00491; A61B 17/320068; A61B 17/3201; A61B 17/3423; A61B 18/02; A61B 1/0005; A61B 1/0008; A61B 1/00154; A61B 1/00177; A61B 1/00183; A61B 1/00188; A61B 1/00195; A61B 1/0125; A61B 1/042; A61B 1/2736; A61B 2010/0225; A61B 2017/00477; A61B 2018/0212; A61B 2090/373; A61B 2090/3735; A61B 2505/05; A61B 34/20; A61B 5/0095; A61B 5/0097; A61B 5/061; A61B 5/076; A61B 5/113; A61B 5/411; A61B 5/416; A61B 5/4233; A61B 5/4504; A61B 5/4519; A61B 5/4523; A61B 5/4533; A61B 5/489; A61B 5/4893; A61B 5/742; A61B 8/0891; A61B 8/12; A61B 8/481; A61B 8/5238; A61B 90/30; A61B 90/50; A61B 90/57; A61B 10/04; A61B 1/00059; A61B 1/0017; A61B 2010/0208; A61B 2010/045; A61B 2017/00699; A61B 2017/00809; A61B 2034/105; A61B 2034/2051; A61B 2034/301; A61B 2090/3925; A61B 2090/3937; A61B 2090/395; A61B 2090/3966; A61B 2562/08; A61B 34/25; A61B 34/30; A61B 5/0088; A61B 5/0261; A61B 5/062; A61B 5/066; A61B 5/082; A61B 5/1076; A61B 5/1107; A61B 5/1127; A61B 5/1128; A61B 5/14542; A61B 5/14556; A61B 5/1459; A61B 5/1468; A61B 5/165; A61B 5/167; A61B 5/4076; A61B 5/412; A61B 5/413; A61B 5/42; A61B 5/4331; A61B 5/7207; A61B 5/7245; A61B 5/743
USPC ....................................................... 359/368
See application file for complete search history.

(56) References Cited

U.S. PATENT DOCUMENTS

2007/0160279 A1* 7/2007 Demos ................ A61B 5/0071
    382/133
2009/0011399 A1* 1/2009 Fischer .................... G01N 1/31
    435/1.1
2017/0370709 A1* 12/2017 Mace ................... G02B 21/008

* cited by examiner

MICROASPIRATION-BASED LUNG WINDOW APPARATUS FOR OBTAINING MICROSCOPIC IMAGE OF IN VIVO LUNG TISSUE AND METHOD FOR OBTAINING IMAGE USING SAME

This is a continuation of International Patent Application No. PCT/KR2016/009720, filed Aug. 31, 2016, which claims priority from Korean Patent Application No. 10-2015-0123216, filed on Aug. 31, 2015, which are hereby incorporated by reference for all purposes as if fully set forth herein.

TECHNICAL FIELD

The present disclosure relates to a microaspiration-based lung window apparatus for obtaining a microscopic image of a lung tissue in vivo and a method for obtaining an image using the same.

BACKGROUND ART

A confocal laser scanning microscope using fluorescent signals is used to observe cellular-level and molecular-level phenomenon.

Unlike other tissues, the pulmonary system periodically moves due to the respiration process and the beating of the heart close to it, thus due to such motion artifacts it is difficult to obtain accurate images when wishing to obtain microscopic images.

Due to this limit, most molecular biological studies are performed in the process of extracting, fixing, and then observing tissues. However, it is difficult to find out, in living animals, changes in blood vessels, or changes or interaction of blood vessels, tissue cells in lung parenchyma, and circulating cells including erythrocytes, leukocytes, and thrombocyte.

Accordingly, it became an important subject to find out interaction between cells and molecular-level structures while physiologically maintaining respiration and circulation of living animals.

To this end, it is required to develop an imaging window that allows for observing a molecular biological mechanism that occurs in a lung system and blood vessels in vivo, and can overcome a motion-artifact of microscopic images obtained through a confocal microscope.

DETAILED DESCRIPTION OF THE INVENTION

Technical Problem

In order to solve these problems in the related art, the present disclosure provides a microaspiration-based lung window apparatus for obtaining a microscopic image of an in vivo lung tissue and a method for obtaining an image using the same, the apparatus and method being able to stably obtain cellular-level and molecular-level microscopic images of a lung tissue in vivo while physiologically maintaining and not interfering with respiration and circulation of an animal.

Technical Solution

According to an embodiment, there is provided a microaspiration-based lung window apparatus for obtaining a microscopic image of a lung tissue in vivo, the apparatus comprising: an open window configured to open in upper and lower parts thereof, have a cover glass placed on the upper part thereof, and have a lung tissue brought in contact with the lower part thereof;
a suction tube configured to extend to a suction device from a side of the open window and make the inside of the open window vacuum; and a tilting mount seat, configured to extend from a side of the open window, in which a tilting mount is placed to maintain the cover glass and an objective lens of a confocal microscope system in parallel.

According to an embodiment, there is provided a microaspiration-based lung window apparatus for obtaining a microscopic image of a lung tissue in vivo, the apparatus consisting of: an open window configured to open in upper and lower parts thereof, have a cover glass placed on the upper part thereof, and have a lung tissue brought in contact with the lower part thereof;
a suction tube configured to extend to a suction device from a side of the open window and make the inside of the open window vacuum; and a tilting mount seat, configured to extend from a side of the open window, in which a tilting mount is placed to maintain the cover glass and an objective lens of a confocal microscope system in parallel.

According to an embodiment, there is provided a microaspiration-based lung window apparatus for obtaining a microscopic image of a lung tissue in vivo, the apparatus essentially consisting of: an open window configured to open in upper and lower parts thereof, have a cover glass placed on the upper part thereof, and have a lung tissue brought in contact with the lower part thereof;
a suction tube configured to extend to a suction device from a side of the open window and make the inside of the open window vacuum; and a tilting mount seat, configured to extend from a side of the open window, in which a tilting mount is placed to maintain the cover glass and an objective lens of a confocal microscope system in parallel.

The open window may have a conical shape of which a diameter is increased from its upper part to its lower part.

The tilting mount seat may have a plurality of fastening holes for coupling the tilting mount.

The open window and the suction tube are formed in a first plate which has a first body and first protrusions having a step with respect to the first body and protrudes from sides of the first body, and
the tilting mount seat is formed in a second plate which has a second body and second protrusions having a step with respect to the second body and joining with the first protrusions.

According to another aspect, there is provided a microaspiration-based lung window apparatus for obtaining a microscopic image of an lung tissue in vivo, the apparatus comprising: a first plate in which an open window and a suction tube are formed, wherein the open window is configured to open in upper and lower parts thereof, have a cover glass placed on the upper part thereof, and have a lung tissue brought in contact with the lower part thereof, wherein the suction tube is configured to extend to a suction device from a side of the open window and make the inside of the open window vacuum; and a second plate, which is configured to join with the first plate, where there is formed a tilting mount seat in which a tilting mount is placed to maintain the cover glass and an objective lens of a confocal microscope system in parallel.

According to another aspect, there is provided a microaspiration-based lung window apparatus for obtaining a microscopic image of an lung tissue in vivo, the apparatus consisting of: a first plate in which an open window and a suction tube are formed, wherein the open window is configured to open in upper and lower parts thereof, have a cover glass placed on the upper part thereof, and have a lung tissue brought in contact with the lower part thereof, wherein the suction tube is configured to extend to a suction device from a side of the open window and make the inside of the open window vacuum; and a second plate, which is configured to join with the first plate, where there is formed a tilting mount seat in which a tilting mount is placed to maintain the cover glass and an objective lens of a confocal microscope system in parallel.

According to another aspect, there is provided a microaspiration-based lung window apparatus for obtaining a microscopic image of an lung tissue in vivo, the apparatus essentially consisting of: a first plate in which an open window and a suction tube are formed, wherein the open window is configured to open in upper and lower parts thereof, have a cover glass placed on the upper part thereof, and have a lung tissue brought in contact with the lower part thereof, wherein the suction tube is configured to extend to a suction device from a side of the open window and make the inside of the open window vacuum; and a second plate, which is configured to join with the first plate, where there is formed a tilting mount seat in which a tilting mount is placed to maintain the cover glass and an objective lens of a confocal microscope system in parallel.

According to another aspect, there is provided a method of obtaining an image using a confocal microscope system and a microscopic aspiration-based lung window apparatus, the method comprising: adjusting the angle of the lung window apparatus by using a tilting mount placed on a tilting mount seat of the lung window apparatus; radiating laser beams having a plurality of wavelengths to a lung tissue through an open window of the lung window apparatus, wherein a cover glass is placed over the upper part of the open window, the lung tissue is brought in contact with the lower part of the open window, a suction tube extending to a suction device is formed on a side of the open window, so as to keep the inside of the open window vacuum; and detecting a fluorescent signal excited in the lung tissue, wherein the cover glass placed over the open window and an objective lens of the confocal microscope system are maintained in parallel in a respiration or circulation process by adjusting the angle of the tilting mount.

According to another aspect, there is provided a method of obtaining an image using a confocal microscope system and a microscopic aspiration-based lung window apparatus, the method consisting of: adjusting the angle of the lung window apparatus by using a tilting mount placed on a tilting mount seat of the lung window apparatus; radiating laser beams having a plurality of wavelengths to a lung tissue through an open window of the lung window apparatus, wherein a cover glass is placed over the upper part of the open window, the lung tissue is brought in contact with the lower part of the open window, a suction tube extending to a suction device is formed on a side of the open window, so as to keep the inside of the open window vacuum; and detecting a fluorescent signal excited in the lung tissue, wherein the cover glass placed over the open window and an objective lens of the confocal microscope system are maintained in parallel in a respiration or circulation process by adjusting the angle of the tilting mount.

According to another aspect, there is provided a method of obtaining an image using a confocal microscope system and a microscopic aspiration-based lung window apparatus, the method essentially consisting of: adjusting the angle of the lung window apparatus by using a tilting mount placed on a tilting mount seat of the lung window apparatus; radiating laser beams having a plurality of wavelengths to a lung tissue through an open window of the lung window apparatus, wherein a cover glass is placed over the upper part of the open window, the lung tissue is brought in contact with the lower part of the open window, a suction tube extending to a suction device is formed on a side of the open window, so as to keep the inside of the open window vacuum; and detecting a fluorescent signal excited in the lung tissue, wherein the cover glass placed over the open window and an objective lens of the confocal microscope system are maintained in parallel in a respiration or circulation process by adjusting the angle of the tilting mount.

The term 'comprising' used herein have the same meaning as terms 'including' or 'characterized by', not excluding additional non-stated apparatuses, components, or steps in an apparatus or a method. The term 'consisting of' excludes additional elements, steps, or components not specifically stated. The term 'essentially consisting of' means including elements, components, or steps that do not actually influence basic characteristics in addition to stated elements, components, or steps in an apparatus or a method.

Advantageous Effects

According to the present disclosure, an open window that is attached to a lung tissue and placed close to an object lens and a seat that extends from the open window and on which a tilting mount is mounted are provided, and the open window and the objective lens can be maintained in parallel during respiration and circulation on an animal, so it is possible to obtain stable images.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

MODE FOR CARRYING OUT THE INVENTION

Figure 1:
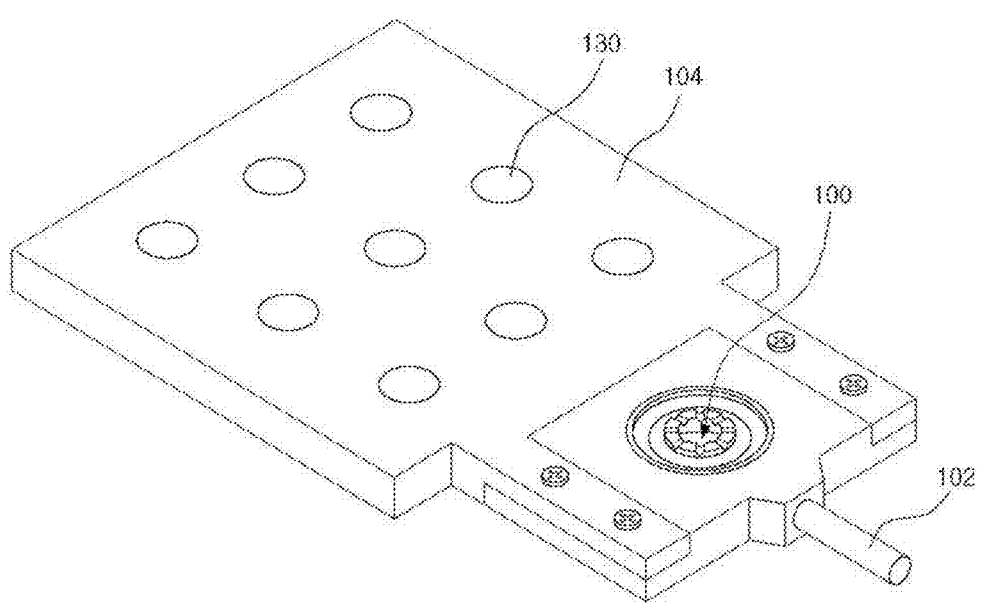
FIG. 1 is a perspective view showing a lung window apparatus according to a preferred embodiment of the present invention.

The present disclosure may be modified in various ways and implemented by various exemplary embodiments, so that specific exemplary embodiments are shown in the drawings and will be described in detail.

However, it is to be understood that the present disclosure is not limited to the specific exemplary embodiments, but includes all modifications, equivalents, and substitutions included in the spirit and the scope of the present disclosure. Reference numerals are assigned to reference components in the following description of drawings.

Hereinafter, exemplary embodiments will be described in detail with reference to the accompanying drawings.

Figure 2:
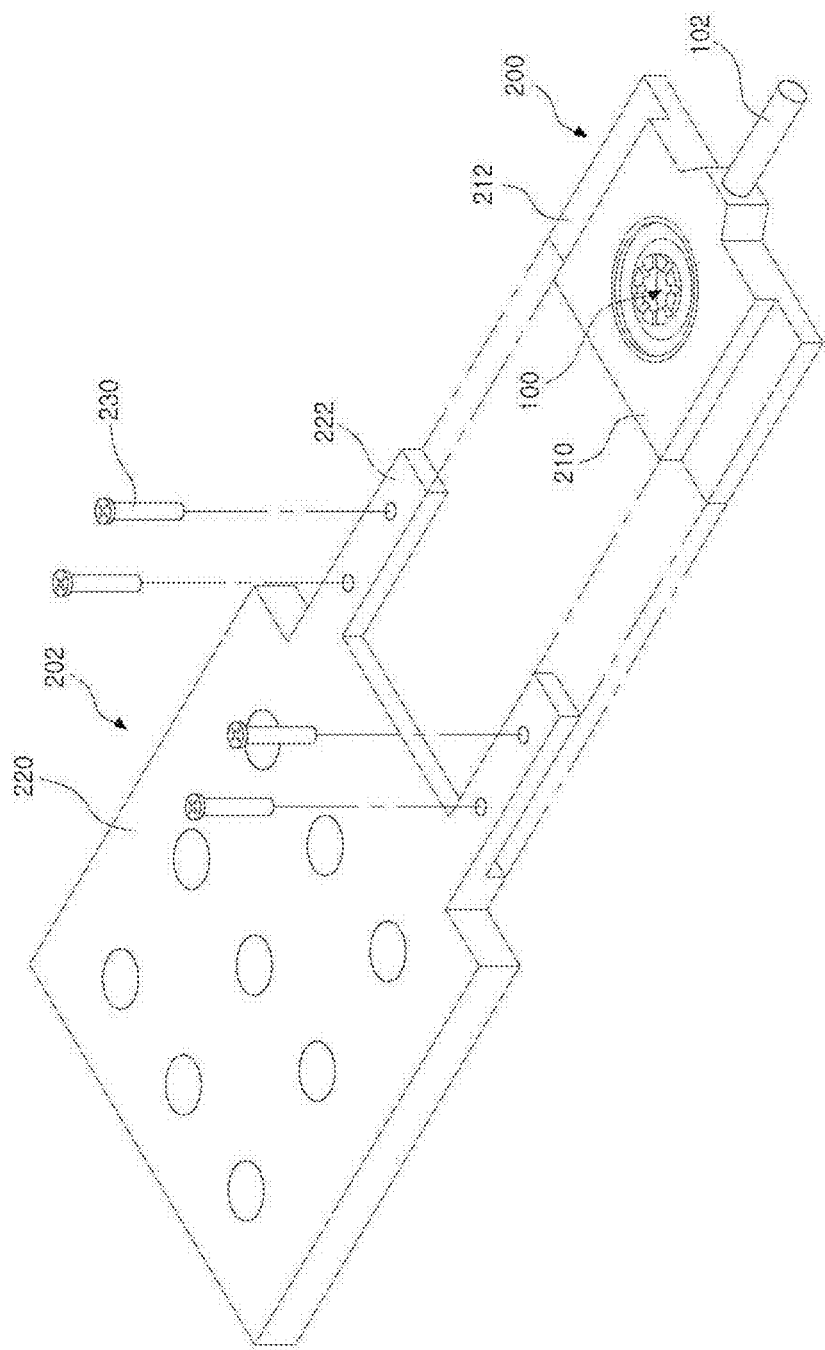
FIG. 2 is a view showing the lung window apparatus according to an embodiment of the present invention when it is separated.
Figure 3:
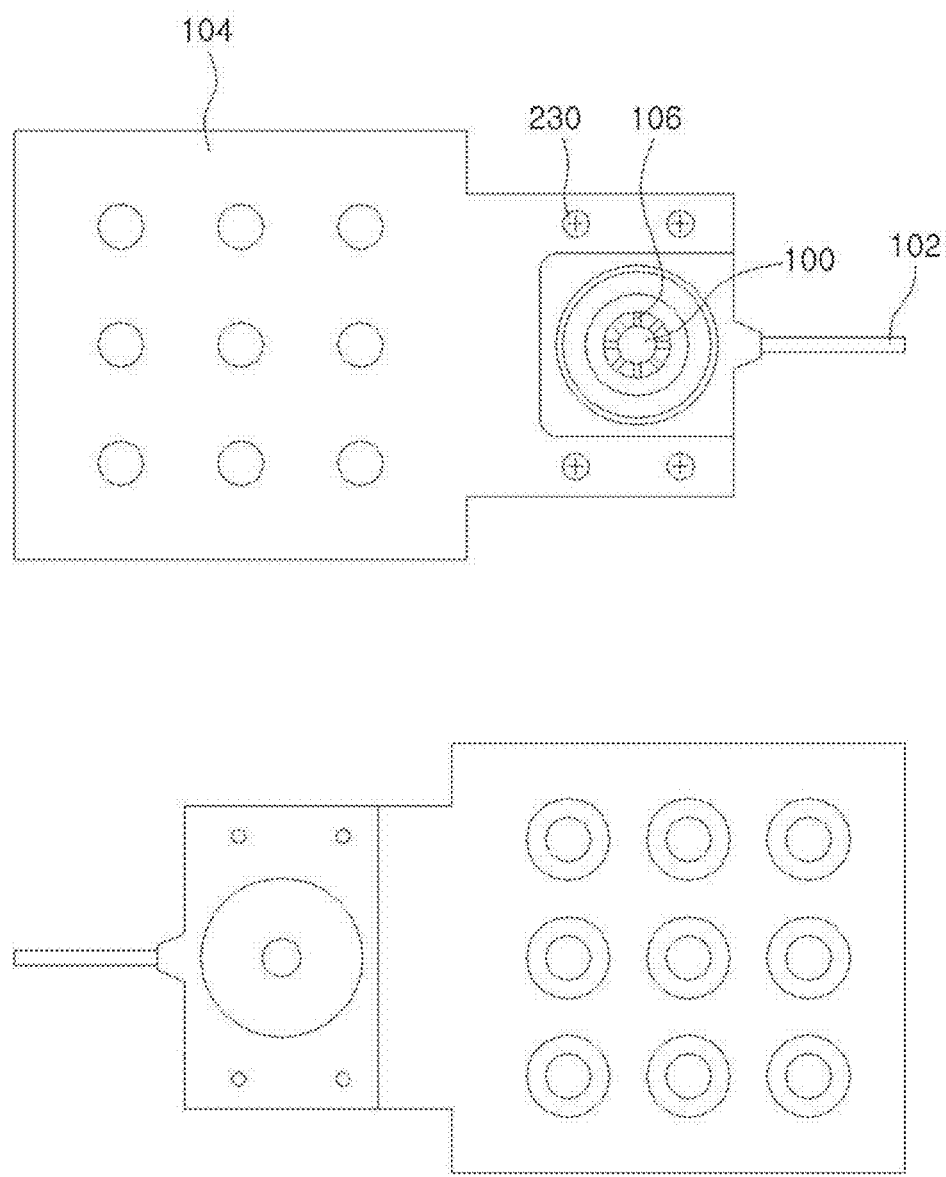
FIG. 3 shows a front view and a bottom view of the lung window apparatus according to an embodiment.
Figure 4:
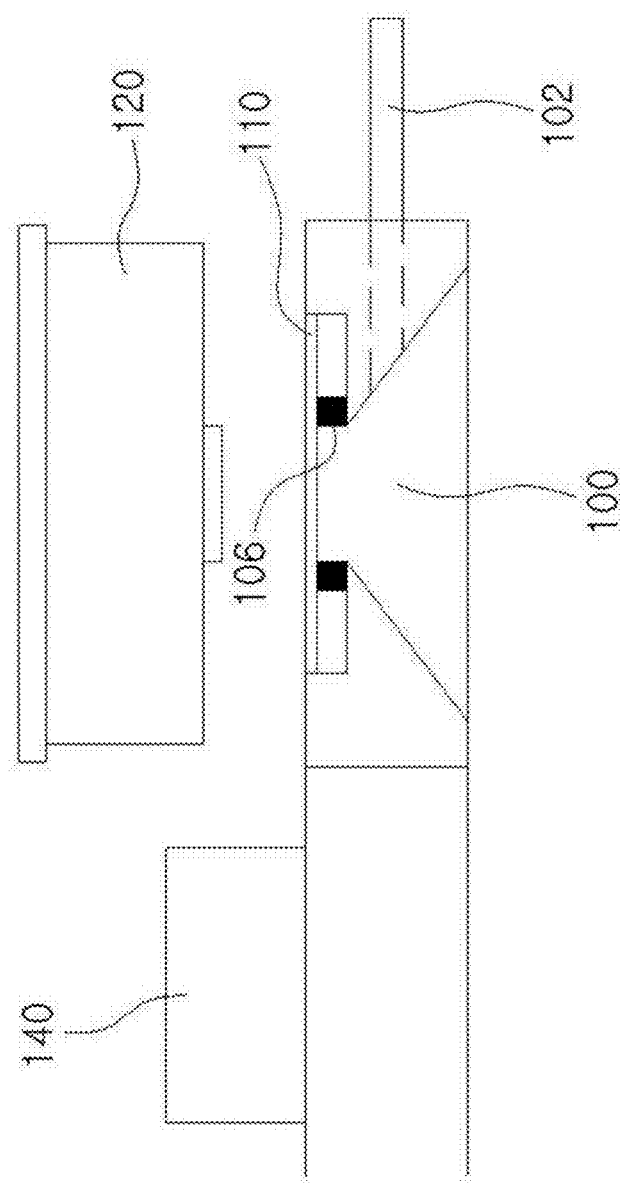
FIG. 4 shows a vertical cross-sectional view of the lung window apparatus according to an embodiment.

FIG. 1 is a perspective view showing a long window apparatus according to an embodiment, FIG. 2 is a view showing the lung window apparatus according to an embodiment when it is separated, FIG. 3 shows a front view and a bottom view of the lung window apparatus according to an embodiment, and FIG. 4 shows a vertical cross-sectional view of the lung window apparatus according to an embodiment.

Referring to FIGS. 1 to 4, a lung window apparatus according to an embodiment may include an open window 100, a suction tube 102, and a tilting mount seat 104.

The open window has a conical shape with open top and bottom and a diameter is increased from its upper part to its lower part.

The open window 100 is brought in contact with a lung tissue on the bottom and a cover glass seat 106 is placed over the open window 100.

When an image is obtained, a cover glass 110 is placed on the cover glass seat 106 and an objective lens 120 is placed over the cover glass 110.

The suction tube 102 extends to a suction device (not shown) from a side of the open window 100.

A cross-section of a lung tissue is brought in contact with the bottom of the open window 100, the cover glass 110 is placed over the open window 100, and the suction tube 102 is placed on a side of the open window 100, so it is possible to keep the inside of the open window 100 vacuum when obtaining an image.

The tilting mount seat 104 extends from a side of the open window 100 and has a plurality of fastening holes 130, and a tilting mount 140 is coupled through at least some of the fastening holes 130.

In the embodiment, the tilting mount 140 is a kinematic tilting mount and maintains the lung window apparatus and the objective lens 120 in parallel by adjusting the angle of the lung window apparatus.

When the objective lent 120 and the cover glass 110 placed over the open window 100 are maintained in parallel by adjusting the angle of the lung window apparatus through the kinematic tilting mount 140, movement of the lung window apparatus can be restricted even with respiration and circulation physiologically maintained, so images can be stably obtained.

According to an embodiment, the lung window apparatus may be provided by combining first plate 200 and a second plate 202, which are individual parts, with each other.

Referring to FIG. 2, it is possible to provide the lung window apparatus comprising the tilting mount seat 104 and the open window 100 by putting the first plate 200 and the second plate 220 such that first protrusions 212 formed on a side of a first body 210 of the first plate 200 and second protrusions 222 formed on a side of a second body 220 of the second plate overlap each other, and then fastening the plates with bolts 230.

The open window 100 is formed in the first body 210 and the tilting mount seat 104 is formed in the second body 220.

According to the embodiment, the first protrusions 212 are smaller in thickness than the first body 220 and the second protrusions 222 are smaller in thickness than the second body 220.

Preferably, the first body 210 and the second body 220 may be the same in thickness, and the entire thickness when the first protrusions 212 and the second protrusions 222 overlap each other may be the same as the thickness of the first body 210 and the second body 220.

The first plate 200 and the second plate 202 have steps, and when the first protrusions 212 and the second protrusion 222 overlap each other, the entire thickness is uniform.

Figure 5:
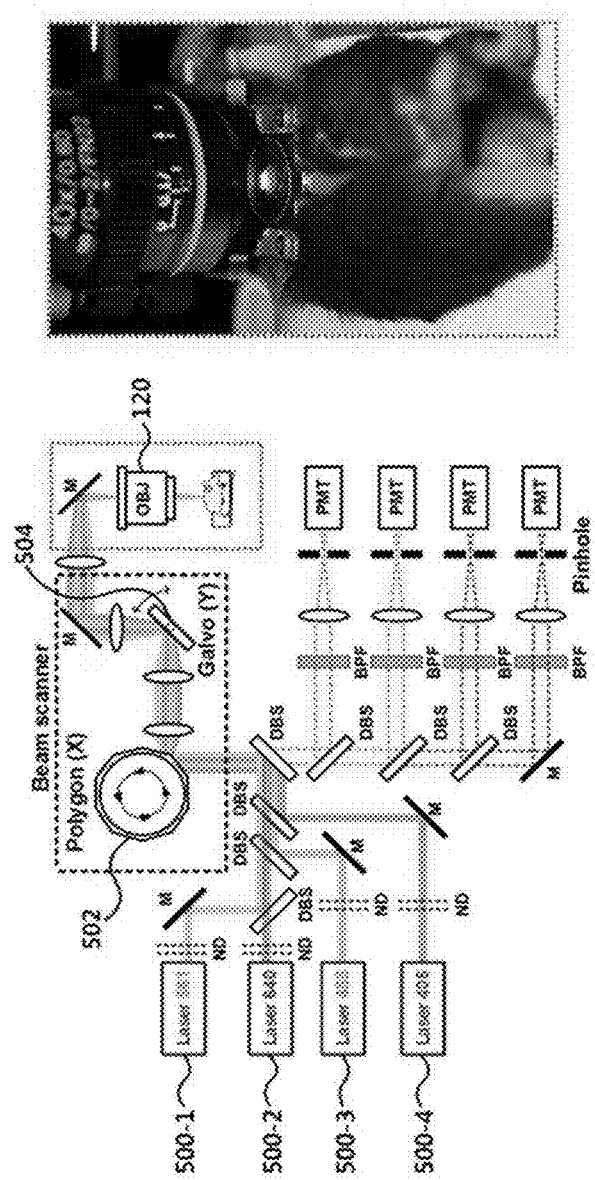
FIG. 5 is a view showing arrangement of a confocal microscope system, the lung window apparatus, and an objective lens according to an embodiment.

FIG. 5 is a view showing the configuration of a confocal microscope system and arrangement of the lung window apparatus and the objective lens according to an embodiment.

A process of obtaining an image according to the embodiment is as follows.

(1) Adjustment of Angle of Lung Window Apparatus

The angle of the lung window apparatus is adjusted using the tilting mount 140 placed on the tilting mount seat 104 of the lung window apparatus.

(2) Emission of Laser Beam

As in FIG. 5, laser beams having a plurality of wavelengths are radiated to a lung tissue through the open window 100 of the lung window apparatus.

(3) Detection of Fluorescent Signal

A fluorescent signal excited in the lung tissue is detected through a detector.

Referring to FIG. 5, the confocal microscopic system according to the embodiment includes four laser sources 500-1 to 500-4 respectively four wavelengths of 405 nm, 488 nm, 561 nm, and 640 nm within the visible light band, a polygonal rotation mirror 502, and a galvanometer mirror 504, and generates an XY raster scanning pattern, using these components.

The confocal microscopic system may comprise a plurality of neutral density filters ND, mirrors M, and Dichroic beam splitters DBS, and beam pass filters BPF and photomultiplier tubes for detecting a fluorescent signal excited in a lung tissue.

Images of a lung tissue were obtained from an actual animal model, using the confocal optical microscope using the microaspiration-based lung window apparatus of the present disclosure.

An optical system was designed to have an observation view of 250×250 $\mu m^2$ at the focus when using a ×40 objective lens (LUCPlanFL, NA0.6; Olympus) and a fluorescent signal was detected and processed by photomultiplier tubes individually and frame grabbers (Matrox, SOLIOS) that are provided for wavelengths such that 2D images having cellular-level resolution and being able to be sectioned in the Z-axial direction could be obtained at a speed of 30 sheets per second.

By attaching the lung window apparatus according to an embodiment to the confocal microscope system and radiating laser beams to a lung tissue through an objective lens, it is possible to obtaining cellular-level images in real time through excited fluorescent signals.

Figure 6A:
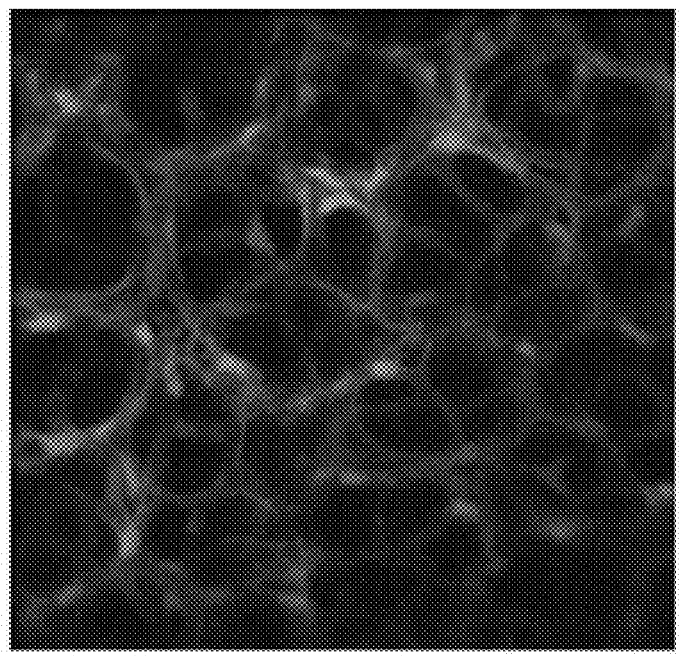
FIGS. 6A-B are views showing lung tissue images obtained using a microaspiration-based lung window apparatus and a confocal microscope system according to an embodiment, where a black circular pulmonary alveoli and a capillary vessel, shown in green in FIG. 6A and red in FIG. 6B, composed of vascular endothelial cells surrounding the lungs are found.
Figure 6B:
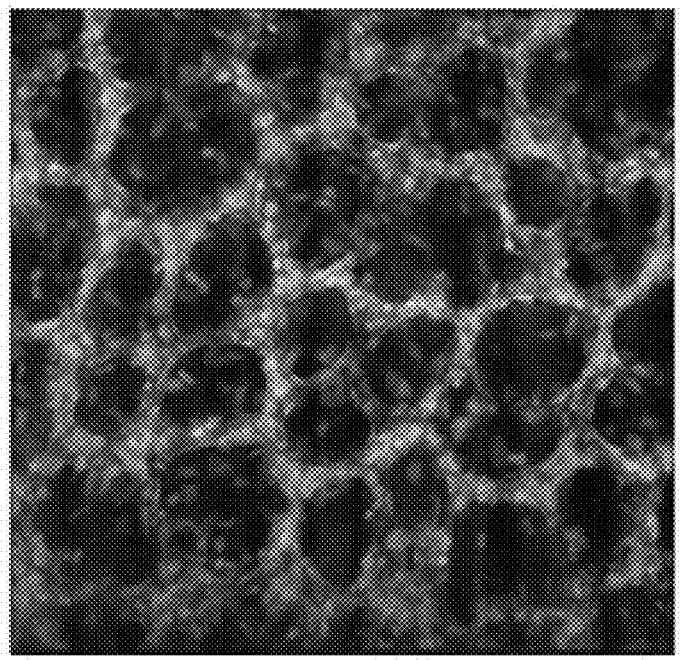

FIGS. 6A-B are views showing lung tissue images obtained using a microaspiration-based lung window apparatus and a confocal microscope system according to an embodiment.

A lung tissue has a pulmonary alveolus and a capillary vessel surrounding the pulmonary alveolus and the capillary vessel has a vascular endothelial cell and a basement membrane covering the vascular endothelial cell.

In order to check first the structure of such a lung, observation was performed on the lungs of a Tie2-GFP mouse having a green fluorescent signal expressed in a Tie2 receptor and an Actin-DsRed & Histone-GFP having a red fluorescent signal expressed in an Actin filament and a green fluorescent signal expressed in Histone, using a confocal microscope system and the lung window apparatus according to the embodiment.

As described above, a black circular pulmonary alveoli and a capillary vessel (green in FIG. 6A and red in FIG. 6B) composed of vascular endothelial cells surrounding the lungs are found.

Further, in a lung tissue, nuclei (green in FIG. 6B) of type I pulmonary cells, type II pulmonary alveoli, and nuclei of macrophages around the pulmonary cells could be found.

Figure 7:
FIG. 7 is a view showing an image obtained by continuously imaging movement of erythrocyte after injecting FITC-Dextran into a C57BL6/J mouse obtained using a microaspiration-based lung window apparatus and a confocal microscope system according to an embodiment.

FIG. 7 is a view showing an image obtained by continuously imaging movement of erythrocyte after injecting FITC-Dextran into a C57BL6/J mouse obtained using a microaspiration-based lung window apparatus and a confocal microscope system according to an embodiment.

An image for observing movement of erythrocyte and leukocyte was checked in consideration of influence on cells in a lung tissue due to microaspiration. An image of erythrocyte contrasted by black was obtained by injecting FITC-Dextran into a blood vessel of the C57BL6/J mouse, and as in FIG. 7, it was found that movement of the erythrocyte was continued and was not influenced by microaspiration.

Figure 8:
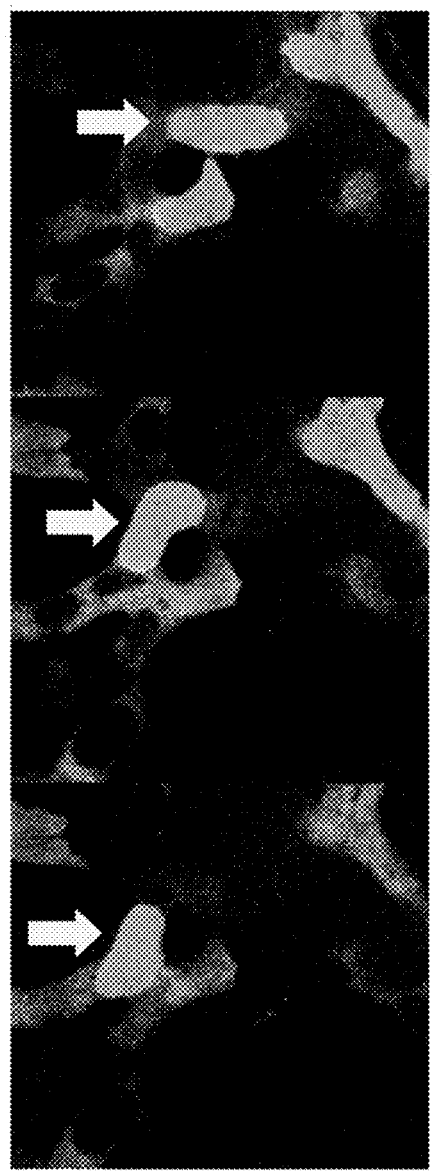
FIG. 8 is a view showing an image obtained by continuously imaging movement of leukocyte in the C57BL6/J mouse obtained using a microaspiration-based lung window apparatus and a confocal microscope system according to an embodiment.

FIG. 8 is a view showing an image obtained by continuously imaging movement of leukocyte in the LysM-GFP mouse obtained using a microaspiration-based lung window apparatus and a confocal microscope system according to an embodiment.

In order to observe movement of leukocyte, injecting TMR-Dextran into a LysM-GFP mouse in which a green fluorescent signal was expressed in LysM protein to show blood vessels with red was performed and then tracing the movement path of the LysM in the blood vessels was performed. As shown in FIG. 8, it was found that movement of leukocyte was also continued and was not influenced by microaspiration.

As described above, by using the lung window apparatus according to the embodiment, it was found that the apparatus was useful for low-invasive and microscopic access to a lung tissue of an animal model without interfering with physiological circulation. Further, it was found that the apparatus was suitable for securing stable images of lung parenchyma and blood vessels and obtaining images for finding out interaction of cells and single cellular-level movement.

Hereinabove, although the present disclosure is described by specific matters such as concrete components, and the like, embodiments, and drawings, they are provided only for assisting in the entire understanding of the present disclosure. Therefore, the present disclosure is not limited to the embodiments. Various modifications and changes may be made by those skilled in the art to which the present disclosure pertains from this description. Therefore, the sprit of the present disclosure should not be limited to the above-described embodiments, and the following claims as well as all modified equally or equivalently to the claims are intended to fall within the scope and spirit of the disclosure.

The invention claimed is:

1. A microaspiration-based lung window apparatus for obtaining a microscopic image of a lung tissue in vivo, the apparatus comprising:
    an open window configured to open in upper and lower parts thereof, have a cover glass placed on the upper part thereof, and have a lung tissue brought in contact with the lower part thereof;
    a suction tube configured to extend to a suction device from a side of the open window and make the inside of the open window vacuum; and
    a tilting mount seat, configured to extend from a side of the open window, in which a tilting mount is placed to maintain the cover glass and an objective lens of a confocal microscope system in parallel.

2. The apparatus of claim 1, wherein the open window has a conical shape of which a diameter is increased from its upper part to its lower part.

3. The apparatus of claim 1, wherein the tilting mount seat has a plurality of fastening holes for coupling the tilting mount.

4. The apparatus of claim 1, wherein the open window and the suction tube are formed in a first plate which has a first body and first protrusions having a step with respect to the first body and protrudes from sides of the first body, and
    the tilting mount seat is formed in a second plate which has a second body and second protrusions having a step with respect to the second body and joining with the first protrusions.

5. A microaspiration-based lung window apparatus for obtaining a microscopic image of a lung tissue in vivo, the apparatus comprising:
    a first plate in which an open window and a suction tube are formed, wherein the open window is configured to open in upper and lower parts thereof, have a cover glass placed on the upper part thereof, and have a lung tissue brought in contact with the lower part thereof, wherein the suction tube is configured to extend to a suction device from a side of the open window and make the inside of the open window vacuum; and
    a second plate, which is configured to join with the first plate, where there is formed a tilting mount seat in which a tilting mount is placed to maintain the cover glass and an objective lens of a confocal microscope system in parallel.

6. The apparatus of claim 5, wherein the first plate has a first body where the open window and the suction tube are formed and first protrusions having a step with respect to the first body and protruding from sides of the first body, and
    the second plate has a second body where the tilting mount seat is formed and second protrusions having a step with respect to the second body and joining with the first protrusions.

7. A method of obtaining an image using a confocal microscope system and a microscopic aspiration-based lung window apparatus, the method comprising:
    adjusting the angle of the lung window apparatus by using a tilting mount placed on a tilting mount seat of the lung window apparatus;
    radiating laser beams having a plurality of wavelengths to a lung tissue through an open window of the lung window apparatus, wherein a cover glass is placed over the upper part of the open window, the lung tissue is brought in contact with the lower part of the open window, a suction tube extending to a suction device is formed on a side of the open window, so as to keep the inside of the open window vacuum; and detecting a fluorescent signal excited in the lung tissue, wherein the cover glass placed over the open window and an objective lens of the confocal microscope system are maintained in parallel in a respiration or circulation process by adjusting the angle of the tilting mount.

* * * * *